United States Patent [19]

Frisco et al.

[11] Patent Number: 4,887,903

[45] Date of Patent: Dec. 19, 1989

[54] APPARATUS FOR READING HEIGHT OF MEASUREMENT COLUMN

[75] Inventors: Frank D. Frisco, Kendall Park; Raymond J. Kadash, Woodbridge; Keith B. Silverman, New Brunswick, all of N.J.

[73] Assignee: Mobil Oil Corporation, New York, N.Y.

[21] Appl. No.: 115,488

[22] Filed: Nov. 2, 1987

[51] Int. Cl.⁴ .................. G01B 11/00; G01B 11/02
[52] U.S. Cl. .................................. 356/372; 33/1 M; 73/440
[58] Field of Search ................ 356/372; 73/437, 440, 73/453, 451; 33/1 M

[56] References Cited

U.S. PATENT DOCUMENTS

| | | | |
|---|---|---|---|
| 2,997,881 | 8/1961 | Hodgkins et al. | 73/440 |
| 3,195,356 | 7/1965 | Pochan | 73/437 |
| 3,761,181 | 9/1973 | Monger et al. | 356/372 |
| 4,186,608 | 2/1980 | Stanonis et al. | 73/451 X |

FOREIGN PATENT DOCUMENTS

| | | | |
|---|---|---|---|
| 2053490 | 2/1981 | United Kingdom | 356/372 |
| 2149095 | 6/1985 | United Kingdom | 356/372 |

*Primary Examiner*—Vincent P. McGraw
*Attorney, Agent, or Firm*—Alexander J. McKillop; Charles J. Speciale

[57] ABSTRACT

An apparatus for determining the position of an object in a vertical column includes a sighting window mounted on a slide movable along a vertical rail. An endless chain extends around a pair of cogged wheels rotatably mounted on rotating shafts at opposite ends of the rail and is connected to the slide so that vertical movement of the sighting window rotates the wheels. One of the wheels is connected to an optical encoder which converts rotation of the wheel to units corresponding to the vertical linear movement of the sighting window. The optical encoder converts the units to an electrical signal which can be delivered to a computer for providing a desired measurement reading base on the position of the object in the column detected by the apparatus. The rail may be mounted on horizontal tracks for movement along a plurality of horizontally spaced columns.

12 Claims, 1 Drawing Sheet

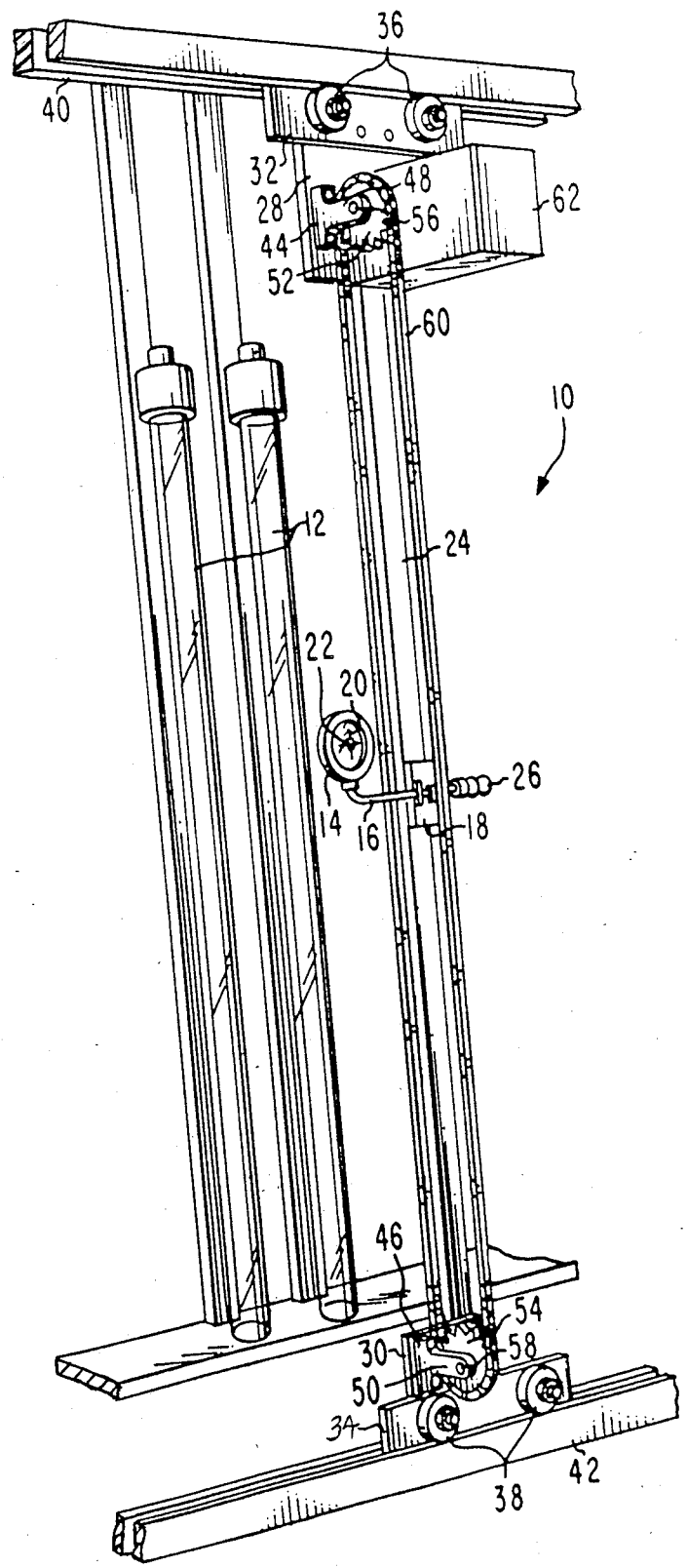

APPARATUS FOR READING HEIGHT OF MEASUREMENT COLUMN

FIELD OF THE INVENTION

The present invention relates to an apparatus for automatically reading the height of a measurement column, such as a density column, and delivery of such measurement to a computer or the like.

BACKGROUND OF THE INVENTION

Many types of measurement equipment use a column of a liquid in which the height of either the liquid or an object in the liquid must be determined. For example, one of the analytical pieces of equipment used in plastics research is a density column. This is used to very accurately measure the specific gravity of small samples of plastic. The density column consists of a graduated glass tube approximately 4 feet long and 1½ inches in diameter. The tube is filled with the appropriate mixture of clear fluids to give a desired density range. As you go lower in the column, the density of the fluid mixture increases. The column is calibrated by using several precision density beads. These beads are pre-calibrated at specific intervals. The beads are dropped into the column and will float at various heights in the column relative to the density of the fluid. The heights are measured by reading a graduated scale on the front of the column. From these readings, a height vs. density profile is generated for the column.

To measure the density of plastic samples, they are placed into the calibrated column. Their final (floating) height is recorded. By going back to the density column profile, the density of the plastic sample can be determined. This process requires a great amount of data manipulation. This is both time consuming and can lead to errors by misreading the fine graduated scale. Therefore, it would be desirable to have an apparatus which would automatically and accurately read the column and provide an electrical signal indicating the height being read. This information would then be delivered to a computer which could automatically profile the column in the calibration mode, and give instant density readings in reading mode.

SUMMARY OF THE INVENTION

An apparatus for automatically determining the height of an object in a vertical column includes sighting means for accurately sighting the object along the column. The sighting means is mounted for movement vertically along the column and includes means for moving the sighting means along the column. The sighting means is connected to means for converting the movement of the sighting means vertically along the column to an electrical signal which corresponds to the vertical position of the sighting means along the column. The electrical signal can be delivered to a computer or the like which can convert the position signal to a desired measurement reading.

BRIEF DESCRIPTION OF THE DRAWING

The Figure of the drawing is a perspective view of the apparatus of the present invention for measuring the position of an object along a vertical column.

DETAILED DESCRIPTION OF PREFERRED EMBODIMENT

Referring to the drawing, there is shown the apparatus of the present invention, generally designated as 10, mounted in front of a plurality of vertical columns 12 mounted in horizontally spaced relation. The columns 12 will be described as density columns, although it should be understood that the apparatus 10 can be used with any type of column which requires the determination of the height of an object, either a liquid or an element in a liquid, in the column. For a density column 12, the apparatus 10 is used to measure the height of a bead or similar element in the liquid in the column.

The apparatus 10 includes a sighting element 14 mounted on the end of an arm 16 extending horizontally from a slide 18. The sighting element 14 includes a window 19, preferably a magnified window, having thereon a pair of cross-lines 20 and an opening 22 or the like therethrough at the junction of the cross-lines 20 for sighting along a column 12. The slide 18 is mounted on a vertical rail 24 and can move vertically along the rail 24. A handle 26 extends horizontally from the slide 18 by which the slide 18 can be moved along the rail 24.

At each end of the vertical rail 24 is a mounting plate 28 and 30 respectively. Wheel support plates 32 and 34 are mounted on the mounting plates 28 and 30 respectively. Wheel support plates 32 and 34 have V-shaped wheels 36 and 38 respectively rotatably mounted thereon. The wheels 36 and 38 ride on horizontal tracks 40 and 42 respectively so that the apparatus 10 can be moved horizontally across the columns 12.

U-shaped brackets 44 and 46 are mounted on the mounting plates 28 and 30 respectively with the arms 48 and 50 of the brackets 44 and 46 extending in the same direction from the mounting plates 28 and 30. The brackets 44 and 46 are in vertical alignment. Cogged wheels 52 and 54 are rotatably mounted between the arms 48 and 50 respectively of the brackets 44 and 46 on shafts 56 and 58 respectively. An endless chain 60 extends around the cogged wheels 52 and 54 and is secured to the slide 18. Thus, movement of the slide 18 along the vertical rail 24 moves the chain 60 which rotates the wheel 52 and 54 and their shafts 56 and 58.

Mounted on the mounting plate 28 is an optical encoder 62 which is connected to the shaft 56 of the cogged wheel 52. The optical encoder is adapted to convert rotation of the shaft into units which indicate vertical movement of the slide 18, which in turn indicates the vertical position of the sighting element 14. A suitable optical encoder is made by the Allen Bradley Company of Milwaukee, Wisc. under Catalogue No. 845B-MAZ1END1LN4. This encoder can convert one turn of the cogged wheel 52 into 1,000 units.

In the operation of the apparatus 10, the apparatus 10 is moved horizontally along the tracks 40 and 42 until it is in front of a desired column 12. Using the handle 26, the operator moves the sighting element 14 vertically along the column 12 until the opening 22 is directly on the object in the column 12, the height of which is being determined. Vertical movement of the slide 18 rotates the cogged wheel 52 and its shaft 56 through the chain 60 so as to operate the optical encoder 62. The optical encoder 62 converts the rotation of the cogged wheel 52 to a signal indicating the vertical position of the sighting element 14 along the column and delivers the signal to a computer. When the operator obtains the desired sighting, he pushes a button, not shown, on the handle 26 which triggers the computer to compute the density of the medium in the column based on the height reading. Instead of a density reading, the computer can provide other types of outputs depending on what the column 12 is being used to measure. Switches, not shown, may be provided along the horizontal tracks 40 or 42 to indicate to the computer the particular column 12 being measured. With the apparatus of the present invention, the computer will be able to read the position of an object in the column 12 to an accuracy of 0.008″ (0.2 mm).

Thus, there is provided by the present invention an apparatus for quickly and accurately measuring the position of an object in a vertical column. The apparatus provides the position information in the form of an electrical signal which can be delivered to a computer which can then convert the measurement to a desired reading.

What is claimed is:

1. An apparatus for automatically determining the height of an object in a vertical column comprising:
   means for sighting the position of the object;
   means for moving said sighting means vertically along said column; and
   means for converting the vertical movement of the sighting means to an electrical signal corresponding to the height of the object in the column.

2. Apparatus in accordance with claim 1 in which the sighting means includes a sight window mounted on a slide movable along a vertical rail.

3. Apparatus in accordance with claim 2 in which the sight window is mounted on an arm projecting from the slide, and a handle is mounted on the slide for moving the slide along the rail.

4. Apparatus in accordance with claim 2 in which the means for converting the movement of the sighting means to an electrical signal includes a pair of wheels each mounted at an opposite end of the rail and means connecting the slide to the wheels to rotate the wheels as the slide moves vertically along the rail.

5. Apparatus in accordance with claim 4 including means for converting the rotation of the wheels to an electrical signal corresponding to the vertical movement of the slide.

6. Apparatus in accordance with claim 5 in which the means for converting the rotation of the wheel to an electrical signal comprises an optical encoder which converts each rotation of the wheel into units corresponding to the linear movement of the slide.

7. Apparatus in accordance with claim 6 in which the wheels are cogged wheels and the means connecting the slide to the wheels is an endless chain extending around the wheels and connected to the slide.

8. Apparatus in accordance with claim 7 in which the vertical rail has a mounting plate at each end thereof, the wheels are mounted on shafts rotatably supported on the mounting plates, and the optical encoder is mounted on one of the mounting plates and is connected to the shaft of the adjacent wheel.

9. Apparatus in accordance with claim 8 in which the mounting plates are slidably mounted on horizontal tracks to allow movement of the apparatus across a plurality of horizontally spaced columns.

10. Apparatus in accordance with claim 9 in which each of the mounting plates has wheels which ride on the tracks.

11. Apparatus in accordance with claim 10 in which the sight window is mounted on an arm projecting from the slide and a handle is mounted on the slide for moving the slide along the rail.

12. Apparatus in accordance with claim 11 in which the sight window is a magnifying window and has a pair of cross-lines thereon.

* * * * *